United States Patent

Boemmel et al.

[11] Patent Number: 6,092,248
[45] Date of Patent: Jul. 25, 2000

[54] PATIENT SUPPORT APPARATUS WITH AIR CUSHION

[75] Inventors: Franz Boemmel; Matthias Gebhardt, both of Erlangen, Germany

[73] Assignee: Siemens Aktiengesellschaft, Munich, Germany

[21] Appl. No.: 09/188,356

[22] Filed: Nov. 10, 1998

[30] Foreign Application Priority Data

Nov. 11, 1997 [DE] Germany .................. 197 49 942

[51] Int. Cl.$^7$ .................................. A61B 5/05
[52] U.S. Cl. ...................... 5/601; 5/81.1; 5/943
[58] Field of Search ................... 5/601, 943, 81.1 R, 5/81.1 HS, 600; 378/209; 108/102; 180/125, 120, 166; 406/86; 414/676

[56] References Cited

U.S. PATENT DOCUMENTS

| | | | |
|---|---|---|---|
| 3,477,839 | 11/1969 | Misson | 414/676 X |
| 3,788,231 | 1/1974 | Bloomfield | 414/676 X |
| 4,805,626 | 2/1989 | Dimassimo et al. | 406/86 X |
| 5,439,341 | 8/1995 | Yamazaki et al. | 414/676 |

OTHER PUBLICATIONS

"Intraoperative Diagnostic and Interventional Magnetic Resonance Imaging in Neurosurgery," Tronnier et al., Neurosurgery, vol. 40, No. 5, May, 1997, pp. 891–902.

*Primary Examiner*—Terry Lee Melius
*Assistant Examiner*—Fredrick Conley
*Attorney, Agent, or Firm*—Hill & Simpson

[57] ABSTRACT

A patient support apparatus has a stationary lower part and a displaceable upper part carrying a patient. The upper part has a guide surface which is curved in sectional plane, and the lower part has a guide surface matched to this curve. Outlet nozzles for air are provided in the guide surface of the lower part so that an air gap and an air cushion are produced between the guide surface of the lower part and the upper part by means of an air flow. The upper part, with a patient thereon, can be displaced in a longitudinal direction, perpendicular to the sectional plane, by riding on the air cushion.

6 Claims, 2 Drawing Sheets

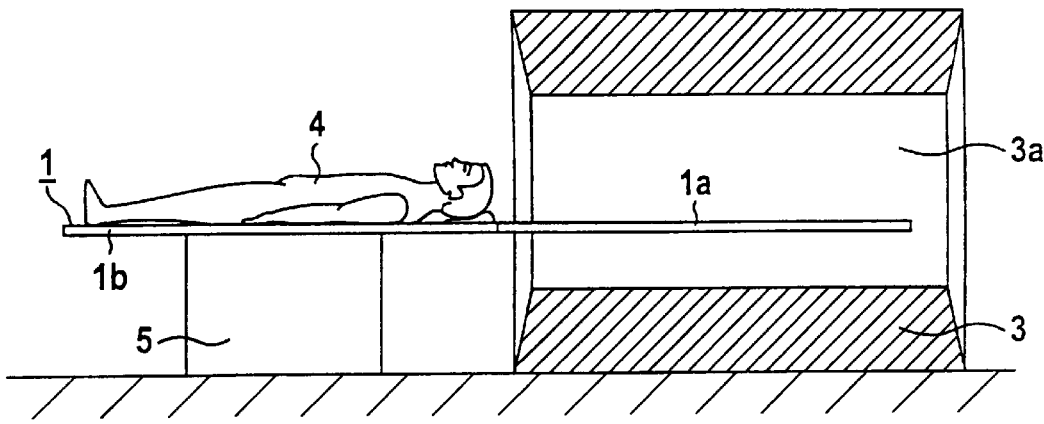
FIG 1
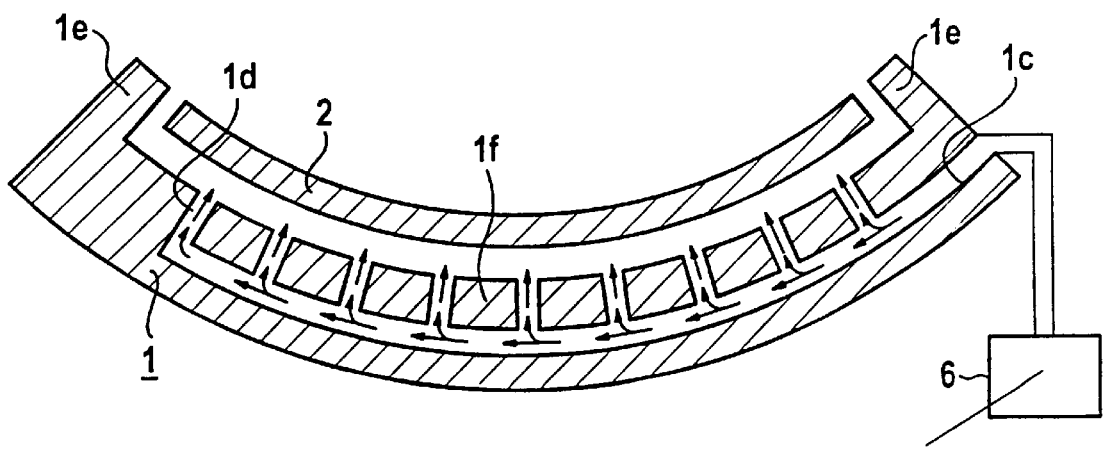
FIG 2  COMPRESSED AIR GENERATOR

PATIENT SUPPORT APPARATUS WITH AIR CUSHION

BACKGROUND OF THE INVENTION

1. Field of the Invention

The present invention relates to a patient support apparatus for medical devices of the type having a stationary lower part and a displaceable upper part.

2. Description of the Prior Art

Patient support apparatuses with which the patient can be displaced rapidly and simply are frequently required in medical technology, particularly for imaging systems. In some systems it is important to build the patient support apparatus as flat as possible. For example, in magnetic resonance tomography devices with magnets in a ring coil arrangement the size of the accessible opening of the magnet largely determines its cost. This is particularly important when the magnetic resonance tomography device is operated with superconductive magnets. With increasing diameter of the examination opening, not only do the coils become larger but a larger cryostat must also be used to cool the coils, given otherwise identical conditions.

In computed tomography as well the costs rise with greater diameter of the patient opening, although to a lesser extent than in magnetic resonance tomography.

Conventional patient support apparatuses are generally equipped with rollers enabling a displacement of the upper part of the bearing apparatus on which the patient lies. These rollers require space in the examination space, however, so that this must be enlarged with the disadvantageous consequences described above. Since the upper part of the patient support apparatus is usually initially placed on a height-adjustable apparatus outside the examination space and is then driven into the examination space, it is costly to construct the patient support apparatus such that a vibration-free transition between the height-adjustable part and the examination space is possible for the upper part.

SUMMARY OF THE INVENTION

It is an object of the invention to provide a patient support apparatus which requires optimally little space in the examination space and enables a vibration-free displacement to the greatest possible extent.

This object is inventively achieved in a patient support apparatus wherein the upper part has a bottom side that is curved in sectional plane, a lower part has a guide surface adapted to this curve, so that a displacement of the upper part is only possible in one direction perpendicular to the sectional plane, outlet nozzles for air disposed in the guide surface of the lower part, and wherein an air gap and an air cushion between the guide surface of the lower part and the upper part are produced by means fo flowing air. This air gap can be kept extremely small, so that the spatial requirement is smaller that for a conventional roller construction. In addition, a possibility for practically vibration-free displacement is enabled, even over coupling points.

The air flow nozzles are preferably connected to a compressed air generator via flow channels integrated in the lower part. Separate air guide hoses can thus be forgone.

In another embodiment the air flow can be switched off for lowering the upper part in an examination position. The upper part can thus be locked in an arbitrary position without separate mechanisms.

DESCRIPTION OF THE DRAWINGS

FIG. 1 is a schematic view through a magnetic resonance tomography device in a longitudinal section.

FIG. 2 is a transverse section through a patient support apparatus in accordance with the invention.

DESCRIPTION OF THE PREFERRED EMBODIMENTS

Figure 3:
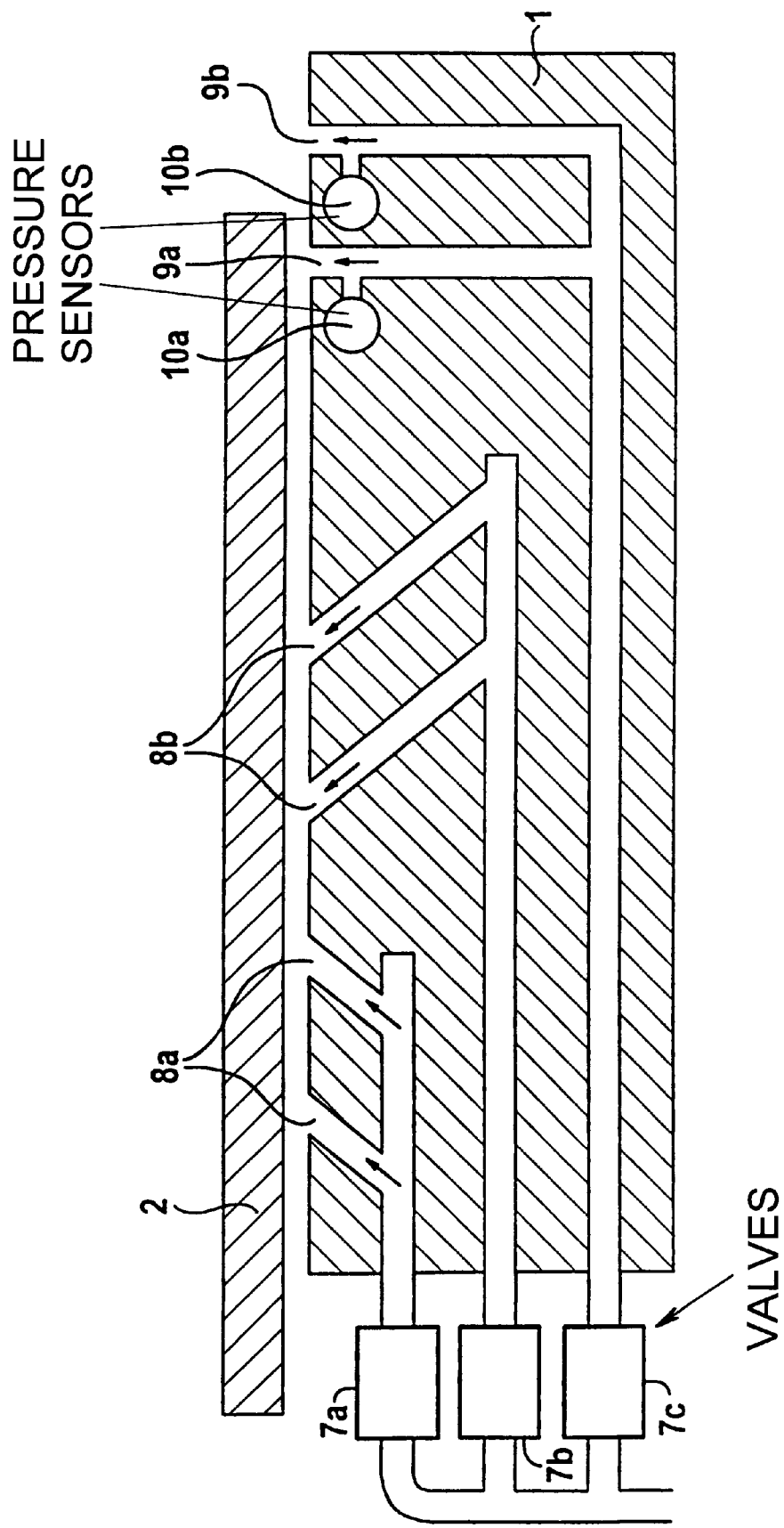
FIG. 3 is a longitudinal section through a patient bearing apparatus of FIG. 2.

FIG. 1 shows a magnetic resonance tomography device in an exemplifying embodiment, wherein an examination space 3a is present in a magnet 3. A patient 4 can be pushed into this examination space 3a on a patient support apparatus, of which only the stationary lower part is depicted in FIG. 1. The stationary lower part 1 includes a part 1a lying within the examination space 3a and fixed therein, and a part 1b lying outside the examination space. The part 1b is mounted on a column 5, for example, and preferably can be lowered for easier loading of the patient onto the support surface.

In the cross-section of the inventive patient support apparatus depicted in FIG. 2 it can be seen that the displaceable upper part 2 on which the patient is placed is in the form of a cylindrical shell. The top side of the lower part 1 and the bottom side of the upper part 2 facing it are matched. Air guide channels 1c are provided in the bottom part 2, with air outlet openings 1d oriented against the bottom side of the upper part 2. The upper part 2 is slightly raised by means of the air stream generated by a compressed air generator 6. A minimal air gap is sufficient to make the upper part 2 with the patient lying thereon freely mobile. The spatial requirement for the arrangement is therefore negligible. A vibration-free displacement is possible at the transition point between the outer lower part 1b and the part 1a lying in the examination region 3a.

Guides 1e are provided on both sides to prevent rolling of the upper part 2 in a perpendicular direction.

Due to the shell-shaped construction of the apparatus, a space-efficient accommodation in the cylindrical inner region of the magnet 3 is possible, and a good lateral guidance of the upper part 2 is also achieved. The shell shape is also favorable for supporting the patient. Since the upper part 2 is supported by an insulating air cushion, or by the lower part 1, practically over its entire surface, it needs only a low structural stability. It therefore can be constructed very thin and thus space-efficient.

Since only a small amount of air must be delivered for the maintenance of a thin insulating air cushion, the air guide channels 1c can be constructed of every diameter. It thus becomes possible to integrate the entire air guidance into an otherwise existing component of the MR device such as a gradient coil or a whole-body resonator. This is also associated with a saving of space. The displacement of the upper part 2 in the longitudinal direction can ensue by hand or in motorized fashion, for example, whereby the smoothness due to the air pillow has a favorable effect. It is also possible to accomplish the displacement by means of the compressed air which is present. Such an embodiment is depicted in FIG. 3 in a longitudinal section. A group of nozzles 8a set obliquely to the right and a group of nozzles 8b set obliquely to the left are respectively provided in the lower part 1.

These groups of nozzles 8a and 8b are respectively supplied with compressed air via respective air valves 7a and 7b. When the valve 7a is opened, the upper part 2 is shifted to the right by the air flowing from the obliquely set nozzles 8a; when the valve 7b is opened, the upper part 2 is shifted to the left by the air flowing from the nozzles 8b.

The position detection of the upper part 2 can ensue by means of back-pressure sensors. Outlet nozzles 9a, 9b for compressed air are therefore present in the lower part 1 for this purpose, the pressure in these outlet nozzles being monitored by pressure sensors 10a, 10b. When the upper part covers either the outlet nozzle 9a or 9b, the air pressure detected by one of the pressure sensors 10a, 10b increases due to the back-pressure, so that the reclining position can be easily detected. It should be noted that for simplicity the air guide channels are depicted on top of one another in the sectional illustration in FIG. 3. Actually all the air guide channels are arranged beside one another in order to construct the lower part 1 in optimally flat and thus space-efficient fashion.

As soon as the patient 4 attains the desired examination position in the examination space 3a by displacement of the upper part 2, the air inflow can be stopped. The upper part 2 thus drops on the lower part 1 and is thus sufficiently fixed for the subsequent examination. Additional locking structures are thus unnecessary.

Although modifications and changes may be suggested by those skilled in the art, it is the intention of the inventor to embody within the patent warranted hereon all changes and modifications as reasonably and properly come within the scope of his contribution to the art.

We claim as our invention:

1. A patient support apparatus for a medical device comprising a stationary lower part;

an upper part, displaceable relative to said lower part, having a top surface adapted to receive a patient and a bottom surface which is curved in a sectional plane;

said stationary lower part having a guide surface matched to the curved bottom surface of said upper part allowing displacement of said upper part only in a direction perpendicular to said sectional place; and a plurality of air outlet nozzles disposed in said guide surface of said lower part and connected to an air source for producing an air gap and an air cushion between said guide surface and said bottom surface of said upper part, said upper part being supported above said lower part exclusively by said air cushion with said upper part being completely out of contact with said lower part.

2. A patient support apparatus as claimed in claim 1 further comprising lateral guides disposed along longitudinal edges of said lower part substantially parallel to the direction of displacement of said upper part.

3. A patient support apparatus as claimed in claim 1 wherein said air source comprises a compressed air generator, and further comprising a plurality of flow channels integrated in said lower part communicating said air outlet nozzles with said compressed air generator.

4. A patient support apparatus as claimed in claim 1 further comprising means for blocking a flow of air from said air source to said air outlet nozzles to allow said bottom surface of said upper part to rest on said guide surface.

5. A patient support apparatus as claimed in claim 1 wherein said air outlet nozzles include at least one set of nozzles which proceed obliquely relative to said guide surface for producing a directed flow of air onto said bottom surface of said upper part for producing a displacement force on said upper part.

6. A patient support apparatus as claimed in claim 1 wherein said air outlet nozzles are disposed in said lower part so as to be successively covered and uncovered by said bottom surface of said upper part as said upper part is displaced, with any of said air outlet nozzles which are covered by said bottom surface of said upper part producing a back pressure, and means for sensing the back pressure in the respective air outlet nozzles for detecting a displacement position of said upper part relative to said guide surface.

* * * * *